(12) United States Patent
Ryan

(10) Patent No.: US 10,213,189 B2
(45) Date of Patent: Feb. 26, 2019

(54) ECHOGENIC ENHANCEMENT FOR A NEEDLE

(71) Applicant: BOSTON SCIENTIFIC SCIMED, INC., Maple Grove, MN (US)

(72) Inventor: Shawn Ryan, Littleton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 137 days.

(21) Appl. No.: 15/351,023

(22) Filed: Nov. 14, 2016

(65) Prior Publication Data

US 2017/0055961 A1   Mar. 2, 2017

Related U.S. Application Data

(63) Continuation of application No. 12/639,573, filed on Dec. 16, 2009, now Pat. No. 9,521,993.

(60) Provisional application No. 61/141,473, filed on Dec. 30, 2008.

(51) Int. Cl.
| | |
|---|---|
| *A61B 10/02* | (2006.01) |
| *A61B 17/34* | (2006.01) |
| *A61B 90/00* | (2016.01) |

(52) U.S. Cl.
CPC ...... *A61B 10/0233* (2013.01); *A61B 17/3403* (2013.01); *A61B 2017/3413* (2013.01); *A61B 2090/3925* (2016.02)

(58) Field of Classification Search
CPC ............ A61B 10/0233; A61B 17/3421; A61B 17/3403; A61M 25/0108
See application file for complete search history.

(56) References Cited

U.S. PATENT DOCUMENTS

| | | | | |
|---|---|---|---|---|
| 4,401,124 A | * | 8/1983 | Guess ................. | A61B 8/0833 600/458 |
| 5,490,521 A | * | 2/1996 | Davis .................. | A61B 8/0833 600/458 |
| 6,053,870 A | * | 4/2000 | Fulton, III ......... | A61B 17/3421 600/458 |

* cited by examiner

*Primary Examiner* — Edelmira Bosques
(74) *Attorney, Agent, or Firm* — Fay Kaplun & Marcin, LLP

(57) ABSTRACT

A needle includes a surface with a plurality of first ultrasound reflecting depressions formed therein. The first depressions are distributed along at least a portion of a length of the needle separated from one another by intervening sections. Each of the first depressions is extending along a curve between first and second ends adjacent to corresponding ones of the intervening sections with troughs at which surfaces of each of the first depressions most closely approach a longitudinal axis of the needle being offset toward the first ends of each of the first depressions.

18 Claims, 3 Drawing Sheets

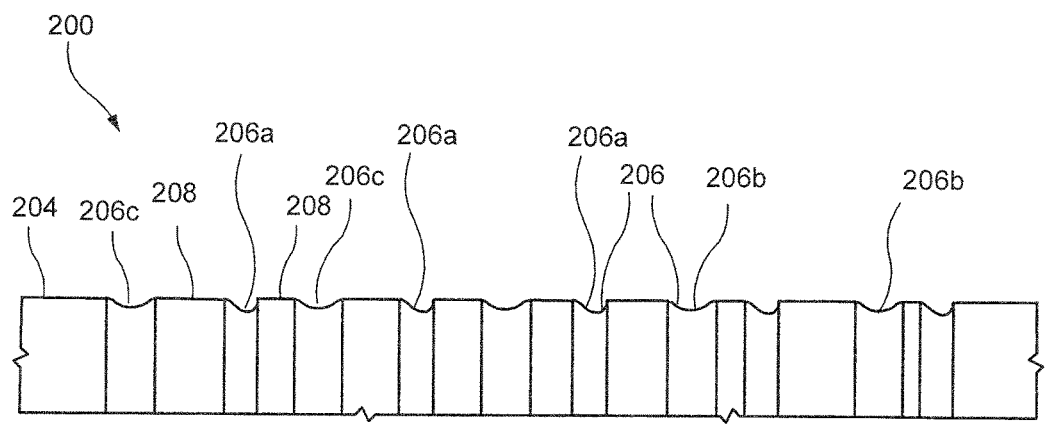
F I G. 4
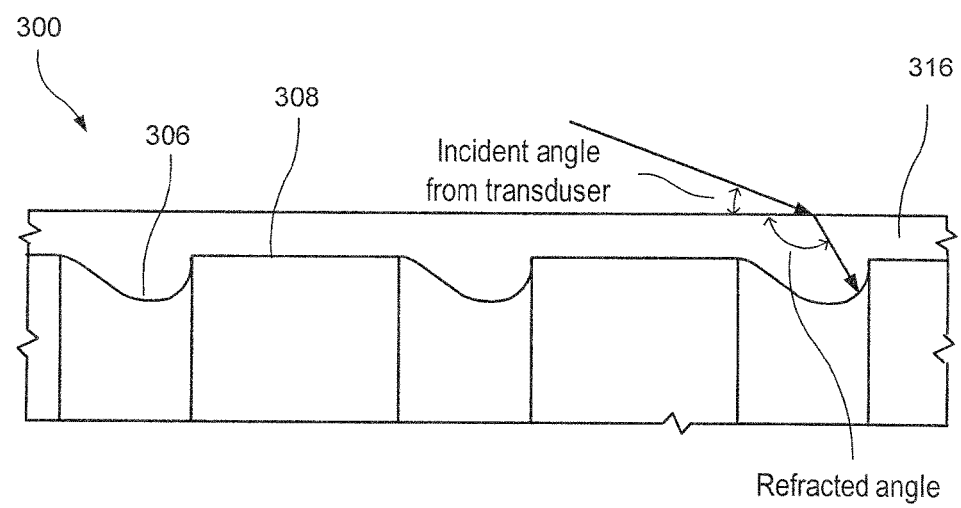
F I G. 5

ECHOGENIC ENHANCEMENT FOR A NEEDLE

PRIORITY CLAIM

This present application is a Continuation of U.S. patent application Ser. No. 12/639,573 filed Dec. 16, 2009, now U.S. Pat. No. 9,521,993; which claims priority to U.S. Provisional Patent Application Ser. No. 61/141,473, entitled "Echogenic Enhancement for a Needle" filed on Dec. 30,2008. All applications/patents are expressly incorporated herein, in their entirety, by reference.

BACKGROUND

Needle biopsies are common procedures for the diagnosis and staging of disease. These procedures are often done under ultrasound guidance to allow physicians performing the procedure to visualize the position of the needle in relation to target and surrounding tissue structures. Thus, the echogenicity of the needle (i.e., the visibility of the needle under ultrasound) often impacts the success of the procedure. The echogenecity may be affected by the size of the needle, a difference between the acoustic impedance of the needle and that of the surrounding tissue, an angle of the needle relative to the transducer, the frequency of the ultrasound energy used and various characteristics of the processing algorithm.

Various techniques have been developed in an attempt to improve the echogenic properties of needles including mechanical treatments of the outer surface of the needle or echogenic coatings. However, the current mechanical treatments involving the creation of discrete shapes repeated along the axis and/or about the circumference of a needle are complex to form. Other mechanical treatments include the formation of circumferential grooves or spirals around the needle. However, these grooves are tuned to only one angle and one frequency such that a slightly different spacing and/or a different frequency may have a significant negative impact on echogenic performance. The application of echogenic coatings increases the complexity of the devices and does not necessarily enhance the performance of these coated devices relative to the mechanical treatments described above. Furthermore, the echogenic properties of these coatings may decay over time.

SUMMARY OF THE INVENTION

The present invention is directed to a needle comprising a surface with a plurality of first ultrasound reflecting depressions formed therein, the first depressions being distributed along at least a portion of a length of the needle separated from one another by intervening sections, each of the first depressions extending along a curve between first and second ends adjacent to corresponding ones of the intervening sections with troughs at which surfaces of each of the first depressions most closely approach a longitudinal axis of the needle being offset toward the first ends of each of the first depressions.

BRIEF DESCRIPTION OF THE DRAWINGS

FIG. 4 shows an enlarged partial side view of a needle with depressions of a variety of shapes and spaces, according to another embodiment of the present invention; and FIG. 5 shows an enlarged partial side view of a needle with depressions along a length of the needle and a coating layer, according to a further embodiment of the present invention.

DETAILED DESCRIPTION

The present invention, which may be further understood with reference to the following description and the appended drawings, relates to devices for conducting biopsies under ultrasound guidance. Exemplary embodiments of the invention are directed to a pattern on an outer surface of a needle such that the needle has enhanced ultrasound visibility, allowing the needle to remain visible at various angles relative to the transducer. It will be understood by those of skill in the art that although the exemplary embodiments are described as a needle, the device may be any medical device that may be seen under ultrasound guidance. It will also be understood by those of skill in the art that since ultrasound is an electromagnetic energy, the patterns described herein, which enhance visibility, may also be used with other energy sources such as, for example, light.

Figure 1:
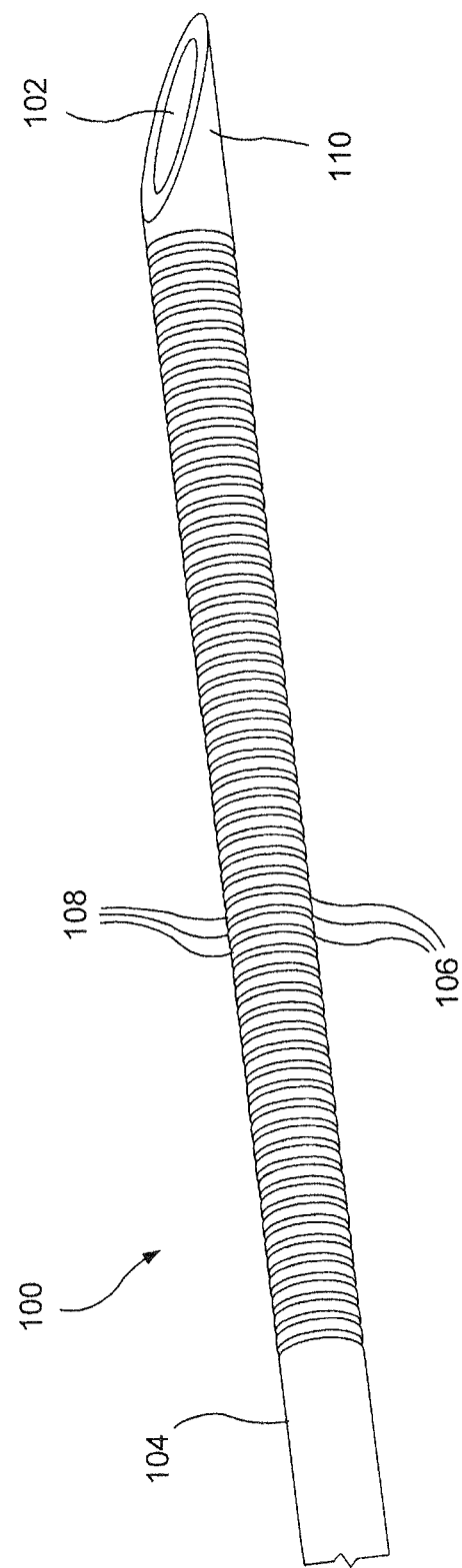
FIG. 1 shows a perspective view of a needle, according to an exemplary embodiment of the present invention.

As shown in FIG. 1, a needle 100 according to an exemplary embodiment of the invention comprises a longitudinal body 118 extending between a distal end 120 and a proximal end 122. An outer surface 104 of the needle 100 includes a plurality of depressions 106 formed along at least a portion of a length of the needle 100 to enhance the visibility of the needle 100 under ultrasound guidance by scattering and reflecting back toward a transducer sound waves incident thereon. The needle 100 will generally comprise a lumen 102 extending therethrough to an opening in a distal tip 110 at a distal end 120 of the needle 100 for collecting target tissue as would be understood by those skilled in the art. As shown in FIG. 1, the tip 110 may be formed by a cut through the needle 100 at an angle relative to a longitudinal axis of the longitudinal body 118. so that a distal-most surface of the needle 100 extends along an angle relative to a longitudinal axis of the needle 100 with an area of the opening to the lumen 102 greater than a cross-sectional area of the lumen 102 within the needle 100.

As would be understood by those skilled in the art, the needle 100 may be formed of any biocompatible material rigid enough to penetrate the tissue targeted by the procedure to which the needle 100 is directed. For example, the needle 100 may be formed of stainless steel or tungsten to enhance the echogencity of the needle. As would be understood by those skilled in the art, tungsten has an acoustic impedance greater than that of stainless steel increasing the difference in acoustic impedance between the needle 100 and the surrounding tissue and thereby enhancing echogenicity. It will be understood in the art, however, that any of a variety of materials may be used to form the needle 100 so long as the material is biocompatible and provides a visible difference in echogenicity as compared to the tissue through which it will be deployed.

Figure 2:
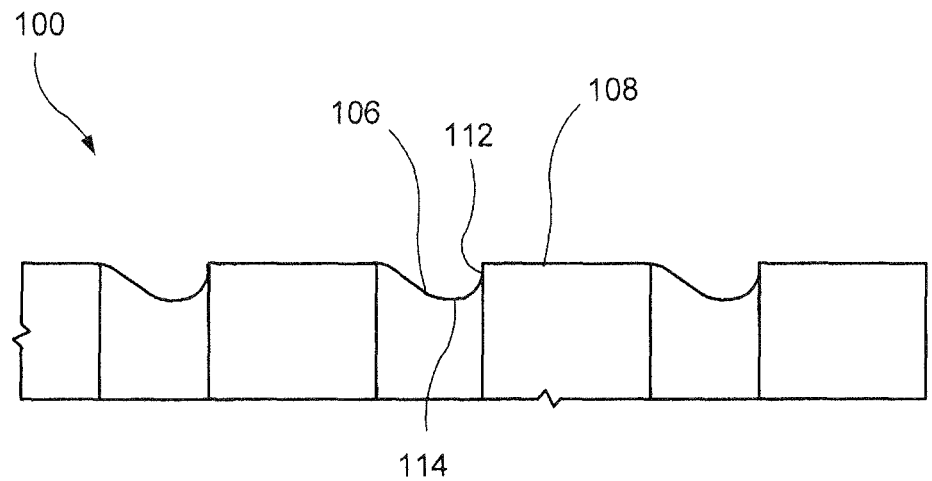
FIG. 2 shows an enlarged partial side view of a needle with depressions along a length of the needle, according to the exemplary embodiment of FIG. 1.

The depressions 106, as shown in the enlarged side view of FIG. 2, are shaped to directly reflect sound waves received over a broad range of angles so that the transducer may be placed in a variety of positions relative to the needle 100. That is, the shapes of the depressions 106 are selected to present at least a part of a face thereof substantially perpendicular to incoming ultrasound radiation over a wide range of incoming angles so that this radiation will be reflected back to the device from which it originated. Thus, a surface of the depression 106 ranges from a steep portion 112 extending from a first end portion abutting a space 108 between adjacent depressions 106 nearly perpendicular to a longitudinal axis of the needle 100 to a trough 114 at which the depression 106 transitions to a shallow portion 116 extending to a second end portion of the depression 106 at an angle less steep than that of the steep portion 112. That is, as the depth of each of the steep portion 112 is equal to that of the shallow portion 116, the trough 114 is closer to the first end than to the second end of the depression 106. At the first end, the surface of the steep portion 112 is, therefore, close to a plane perpendicular to a longitudinal axis of the needle 100 sloping slightly toward a plane parallel to the longitudinal axis. Thus, at least a portion of sound waves from a transducer positioned anywhere in the range of slightly more than 0° to close to 90°, relative to a longitudinal axis of the needle 100 will impact a portion of the depression 106 which is substantially perpendicular to a front of the wave sending the wave directly back to the transducer. The steep portion 112 is positioned to reflect waves back to a transducer aimed nearly parallel (close to 0°) to the needle 100 while the shallow portion is oriented to reflect waves back to a transducer positioned substantially perpendicular to the longitudinal axis (close to 90°) of the needle 100 while the gradual transition between these portions provides surfaces oriented to reflect back to a transducer ultrasound radiation impinging on the needle 100 at any angle between these extremes. It will be understood by those of skill in the art that where the transducer is positioned proximally of the distal end 120 of the needle 100, the steep portion 112 may face proximally such that the sound waves reflect over a broad range of needle-transducer angles.

In a preferred embodiment, each depression 106 extends around an entire circumference of the needle 100. However, it will be understood by those skilled in the art that the depression 106 may extend around only a portion of the circumference of the needle 100 or may be configured as a slot on the outer surface 104 of the needle 100. A space 108 which is substantially flat along a length of the needle 100 is located between each pair of adjacent depressions 106. In the embodiment shown in FIGS. 1 and 2, the depressions 106 are substantially evenly spaced such that each space 108 is equal in length. However, it will also be understood by those of skill in the art that the length of each space 108 may vary along the length of the needle 100. Although the needle 100 is described as being substantially cylindrical, it will be understood by those of skill in the art that the needle 100 may take a variety of shapes so long as it includes a plurality of depressions 106 about at least a portion of a perimeter of the outer surface 104.

It will be understood by those of skill in the art that the features of the needle 100, as described above may also be included in other medical devices that may be viewed under ultrasound guidance. For example, in another embodiment, a sheath, which may be slidable along a portion of a length of a needle may include a pattern substantially similar to the pattern formed by the depressions 106 on the needle 100. In another embodiment, a stylet, which may be slidable through a lumen of a needle to prevent non-target tissue from entering the lumen may be formed with a pattern substantially similar to the pattern formed by the depressions 106 on the needle 100.

Figure 3:
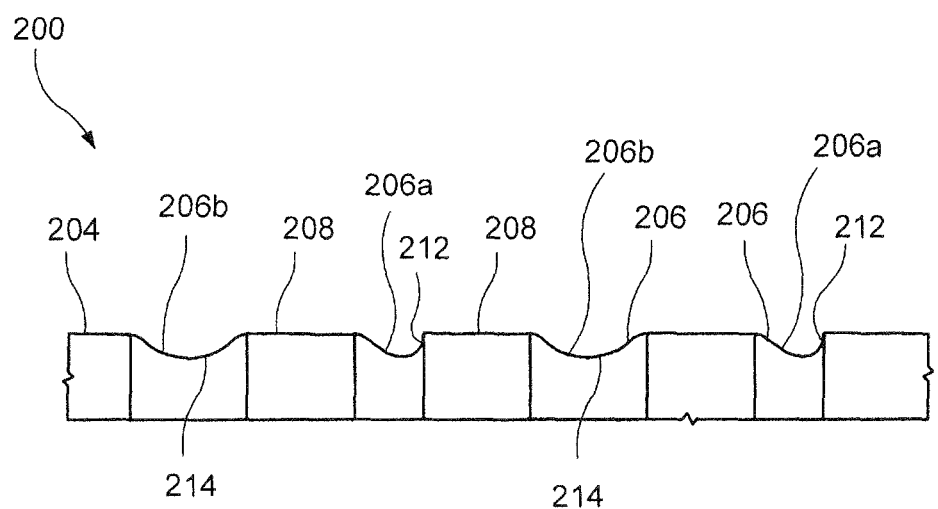
FIG. 3 shows an enlarged partial side view of a needle with depressions of a variety of shapes, according to a further embodiment of the present invention.

A needle 200 according to another embodiment of the invention is substantially the same as the needle 100 described above except that the depressions 206 of the needle 200 are not all of the same shape. For example, the depressions 206 include a plurality of first depressions 206a each of which includes a steep portion 212 oriented to more effectively reflect energy back to a transducer oriented substantially parallel to the needle 200 from the steep portion 212 while each of a plurality of second depressions 206b is shaped as a shallow bowl 214 oriented to more effectively reflect energy to a transducer oriented at a steeper angle relative to the longitudinal axis of the needle 200 (at an angle close to 90° relative to the needle 200). In the embodiment of the needle 200 shown in FIG. 3, each of the first depressions 206a is located between a pair of second depressions 206b are separated by a space 208 which is substantially flat along a length of the needle 200. As described above in regard to the needle 100, the spaces 208 of the needle 200 are substantially equal in size. However, it will be understood by those of skill in the art that the various depressions 206a, 206b may be separated by spaces 208 of varying size, as shown in FIG. 4. It will also be understood by those of skill in the art that the different sizes of the spaces 208 may further tune the response to the sound waves at different angles. Furthermore, those skilled in the art will understand that more than 2 shapes of depressions 206 may be included in the needle 200. For example, as shown in Fig. 4, a plurality of first depressions 206a may be oriented to effectively reflect energy delivered from a probe angled between 0 and 30° relative to the longitudinal axis of the needle 200 while a plurality of second depressions 206b is oriented to effectively reflect energy delivered from a probe angled between 30 and 60° relative to the longitudinal axis and a plurality of third depressions 206c is oriented to effectively reflect energy delivered from a probe angled between 60 and 90° relative to the longitudinal axis.

In a further embodiment of the present invention, as shown in FIG. 5, a needle 300, which may be substantially similar to either of the needles 100 and 200 described above, further comprises a coating layer 316 covering a plurality of depressions 306. Although FIG. 5 shows the needle 300 including depressions 306 of a single shape as in the needle 100, it will be understood by those of skill in the art that the coating layer 316 may be included on any of the needle embodiments described above with any variety of depression shapes and spacings. The coating layer 316 may be formed of a material having an acoustic impedance similar to that of the body tissue within which the needle 300 is to be deployed, but with a lower speed of sound transmission therethrough. This difference in the speed of sound transmission through the tissue and the coating layer 316 refracts the sound waves toward the needle 300, steepening their angle of impact and improving the amount of acoustic energy reflected back to the transducer. An example of a coating layer that may be used is PTFE, which has a lower speed of sound, resulting in the refracted sound waves. A depth of the coating 316 may also be varied to optimize constructive interference and minimize destructive interference between incoming sound waves and reflected sound waves leaving the surface 318 of the coating 316.

The embodiments of the present invention, as described above, may be easily manufactured using a simple tool. For example, the depressions 106 may be formed in the needle 100 using a tool with a protrusion a profile of which matches a desired shape of the depression 106. The tool may be rotated about a circumference, or a part of a circumference, of the needle 100 with the protrusion contacting the outer surface 104 to form the depressions 106 in the longitudinal body 118 the needle 100 as would be understood by those skilled in the art. Alternatively, instead of rotating the tool about the needle 100, the needle 100 may be rotated about a longitudinal axis of the needle while the tool remains stationary such that the protrusion contacts the outer surface 104 of th needle 100. The plurality of depressions 106 may be formed by simply moving the tool along the longitudinal axis of the needle 100 or by moving the needle 100 along the longitudinal axis, by a desired distance of the space 108, and rotating the tool or the needle 100 as described above. This may be repeated until a desired number of depressions 106 have been formed. Alternatively, a tool may include multiple protrusions to form the desired number of depressions 106 in one operation or in a reduced number of operations. For example, a tool to form a needle such as the needle 200 may include a first protrusion having a shape corresponding to the desired shape of the first depressions 206a while a second protrusion has a shape corresponding to a desired shape of the second depressions 206b, etc.

Alternatively, patterns formed by the depressions 106, 206, 306 may be applied to the needles 100, 200, 300, respectively, in the form of rings or other similar elements applied around at least a portion of the outer surfaces of the needles 100, 200 and 300. In another embodiment, a press may be used to stamp the needles with the depressions 106, 206, 306 to form the desired patterns on the needles 100, 200 and 300. In another embodiment, the depressions 106, 206 may be formed by laser micro-machining or by using an EDM process. However, it will be understood by those of skill in the art that any of a variety of methods may be used for forming any of the depressions 106, 206, 306 in the needles 100, 200, 300. As would be understood by those skilled in the art, once the depressions 306 have been formed by any of the above-described methods, the needle 300 may be coated with a desired thickness of the selected material to form the coating 306 using any known technique.

It will be apparent to those skilled in the art that various modifications and variations can be made in the structure and methodology of the present invention, without departing from the spirit or scope of the invention. Thus, it is intended that the present invention cover the modifications and variations of this invention provided that they come within the scope of the appended claims and their equivalents.

What is claimed is:

1. A needle, comprising:
a longitudinal body extending between a proximal end and a distal end and including a lumen extending therethrough, an outer surface of the body including a plurality of first ultrasound reflecting depressions distributed along at least a portion of a length of the body separated from one another by intervening sections, each of the first depressions extending along a longitudinal axis of the needle from a first end to a second end and including a steep slope portion oriented to reflect ultrasound waves to a first transducer, a shallow slope portion oriented to reflect ultrasound waves back to a second transducer, and a trough including a gradual transition between the steep and shallow slope portions, the trough including an inner surface oriented to reflect ultrasound waves back to a third transducer positioned at an angle between the first and second transducers.

2. The needle of claim 1, wherein the steep slope portion of each of the first depressions is at the first end.

3. The needle of claim 1, wherein the shallow slope portion of the each of the first depressions is at the second end.

4. The needle of claim 1, wherein at each of the first ends, the steep slope gradually transitions to extend substantially perpendicular to the longitudinal axis of the needle.

5. The needle of claim 1, further comprising a tip located at the distal end of the needle, the tip being formed angled relative to the longitudinal axis of the needle and adapted to receive therein bodily tissue penetrated by the needle.

6. The needle of claim 1, wherein each of the first depressions extends around an entire circumference of the needle.

7. The needle of claim 1, wherein each of the first depressions extends around only a portion of a circumference of the needle.

8. The needle of claim 1, wherein the first end of each of the first depressions is at a distal end thereof.

9. The needle of claim 1, further comprising a plurality of second ultrasound reflecting depressions distributed along at least a further portion of the length of the needle separated from one another by the intervening sections, each of the second depressions extending along a curve between first and second ends adjacent to corresponding ones of the intervening sections with troughs at which surfaces of each of the second depressions most closely approach the longitudinal axis of the needle being offset toward the second ends of each of the second depressions.

10. The needle of claim 9, wherein the second end of each of the second depressions is at a proximal end thereof.

11. The needle of claim 9, wherein lengths of the intervening sections vary along the needle.

12. The needle of claim 1, wherein the intervening sections are substantially equal in length.

13. The needle of claim 1, further comprising a plurality of third ultrasound reflecting depressions distributed along at least a further portion of the length of the needle separated from one another by the intervening sections, each of the third depressions extending along a curve between first and second ends adjacent to corresponding ones of the intervening sections with troughs at which surfaces of each of the third depressions most closely approach the longitudinal axis of the needle being substantially centered between the first and second ends of each of the third depressions.

14. The needle of claim 13, wherein the first and third depression alternate along the length of the needle.

15. The needle of claim 1, wherein the body is formed of one of stainless steel and tungsten.

16. The needle of claim 1, further comprising a coating covering at least a portion of the needle, a material of the coating layer having an acoustic impedance selected to substantially match an acoustic impedance of bodily tissue within which the needle is to be used.

17. The needle of claim 16, wherein a speed of sound through the material of the coating layer is substantially less than that through the bodily tissue within which the needle is to be used.

18. A medical device, comprising:
a longitudinal body extending between a proximal end and a distal end and including a lumen extending therethrough, an outer surface of the body including a plurality of first ultrasound reflecting depressions distributed along at least a portion of a length of the body separated from one another by intervening sections, each of the first depressions extending along a longitudinal axis of the device from a first end to a second end and including a steep slope portion oriented to reflect ultrasound waves to a first transducer, a shallow slope portion oriented to reflect ultrasound waves to a second transducer separated from the first transducer and a trough including a gradual transition between the steep and shallow slope portions, the trough including an inner surface oriented to reflect ultrasound waves to a third transducer positioned between the first and second transducers.

* * * * *